United States Patent [19]

Paxa

[11] Patent Number: 4,534,342
[45] Date of Patent: Aug. 13, 1985

[54] NOSE BANDAGE

[76] Inventor: Charles Paxa, 1200 Lyan Ave., Wayzata, Minn. 55391

[21] Appl. No.: 594,208

[22] Filed: Mar. 28, 1984

[51] Int. Cl.³ .............................................. A61F 5/04
[52] U.S. Cl. .................................. 128/163; 128/89 R
[58] Field of Search ................... 128/163, 89 R, 89 A, 128/76 C

[56] References Cited

U.S. PATENT DOCUMENTS 4,213,452  7/1980  Shippert ............................... 128/76
4,274,402  6/1981  Shippert ............................... 128/89

FOREIGN PATENT DOCUMENTS 7807130 of 1979 France ................................ 128/342

OTHER PUBLICATIONS

Nasal Splint, Conco Catalog, p. 12, 10-10-72.

Primary Examiner—John D. Yasko
Assistant Examiner—Christa K. Scott
Attorney, Agent, or Firm—Hugh D. Jaeger

[57] ABSTRACT

Nose bandage for nasal dressing of a foam, woven adhesive material, cloth, or porous or non-porous flexible material, including an adhesive coating one side thereof with a protective strip. The nose bandage assumes a geometrical configuration of opposing infra orbital portions, opposing side arm portions, and a connecting bridge between the infra orbital portion and side arm portion. Two perforated holes are provided for nasal passages. The nose bandage is one piece and allows for unilateral or bilateral nasal occlusions. The nose bandage can also be used for securement of packing in the nose, as well as an external nasal dressing.

5 Claims, 4 Drawing Figures

NOSE BANDAGE

BACKGROUND OF THE INVENTION

1. Field of the Invention

The present invention pertains to a surgical dressing, and more particularly pertains to a bandage for the nose.

2. Description of the Prior Art

In the past, bandaging the nose has been one of the most peculiar outwardly extending human appendages to bandage. Every nose of an individual seems to take on a unique configuration; and heretofore, there previously have not been any prior art nose bandages available.

In the past, the medical personal would utilize a series of adhesive tape segments, or in the alternative a series of Band-Aid like members. These bandages would be taped at all angles about the nose presenting a very unsightly configuration of surgical dressings. This would cause, not only personal discomfort, but personal and psychological embarrassment to the individual whose nose was taped.

The present invention overcomes the disadvantages of the prior art by providing a nose bandage which is one piece in design, of a predetermined geometrical shape which provides that one configuration fits all noses, and solves the problems of the prior art, and serving the nose packing better.

SUMMARY OF THE INVENTION

The general purpose of the present invention is to provide a nose bandage which is one piece and provides secure coverage in either unilateral or bilateral nasal occlusions. The nose bandage can be used to retain nasal packing or other nasal occlusion devices. The nose bandage also provides for nasal-facial protective coverings for the care of external nasal-facial injuries.

According to one embodiment of the present invention, there is provided a nose bandage of foam, cloth, porous flexible material, woven adhesive material, or the like, which includes opposing infra orbital portions, opposing side arms, and a connecting bridge therebetween where the geometrical configuration of the infra orbital portions include parallel orbital sides and outwardly curved opposing sides, the opposing side arms include parallel arm sides and outwardly curved opposing sides, two perforated holes are provided as nasal passages in the center mid portion of the opposing side arms, and there is an adhesive coating with a protective strip provided on one side of the bandage for securing over and about the skin of the infra orbital portion of the face.

Significant aspects and features of the present invention include a nose bandage which provides for ease of application and use of a suitable material as nasal dressing.

Another significant aspect and feature of the present invention is a nose bandage which provides for banding of unilateral or bilateral nasal occlusion. This bandage provides for securement of packing in the nose, which has not previously been available which leads to patient comfort and safety in medical treatment. The nose bandage can also be used for external nasal dressings.

A further significant aspect and feature of the present invention is a nose bandage which is cosmetically acceptable, thereby being psychologically acceptable. The nose bandage provides for ease of application, geometrically configured so to be balanced about the face and for patient comfort.

Having thus described the embodiments of the present invention, it is the principal object hereof to provide a nose bandage as a nasal-facial dressing providing for secure coverage in either unilateral or bilateral nasal occlusions.

One object of the present invention is to provide a nose bandage which can be manufactured in different sizes, such as small, medium, and large, for different sized noses.

Another object of the present invention is to provide a nose bandage which is in effect a Band-Aid application for use, such as in first aid kits, home use, and in schools.

A further object of the present invention is to provide a nose bandage which can be individually packaged for sterile purposes.

DESCRIPTION OF THE PREFERRED EMBODIMENTS

Figure 1:
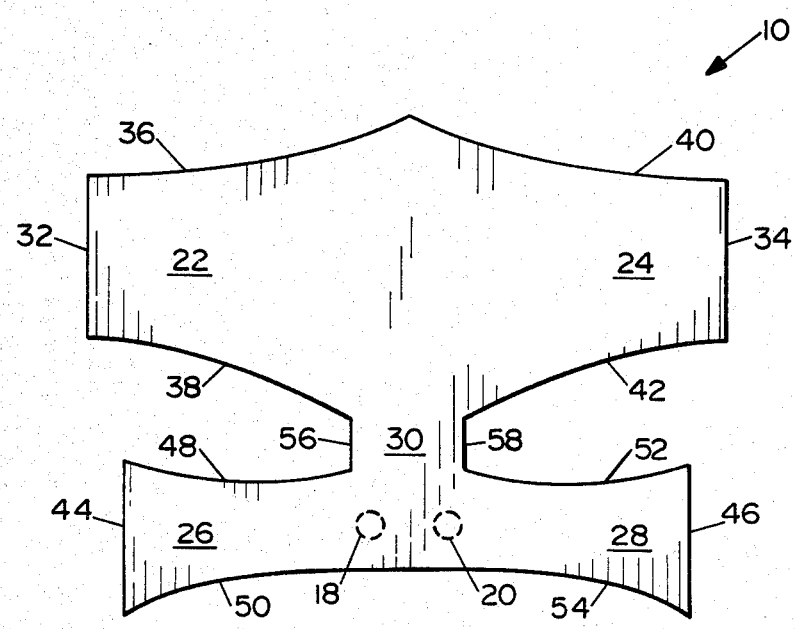
FIG. 1 illustrates a plan view of a nose bandage, the present invention.
Figure 2:
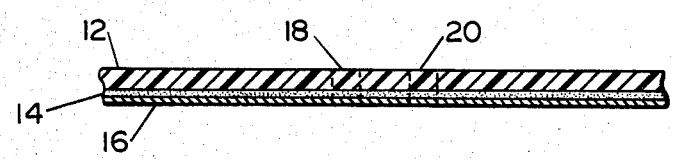
FIG. 2 illustrates a cross sectional side view.

FIG. 1 illustrates a plan view of a nose bandage 10, the nose bandage being made of thin plastic foam, such as 1/16" to ⅛", woven adhesive material, plastic, breathable cloth, or the like material 12 suitable for surgical dressings. The material can be flesh tone, black, brown, or yellow to blend with a person's skin. The nose bandage will include an adhesive coating 14 over one side of the nose bandage material 12, and a protective strip 16 over the adhesive coating 14, as also illustrated in FIG. 2. The nose bandage 10 includes at least two round nasal perforated passages 18 and 20. More than two holes can be provided, or in the alternative, a plurality of smaller holes at each nasal passage can be provided. The nasal passages 18 and 20 are preferably perforated into the material 12 of the nose bandage 10 so that the perforated passages can be punched out by the medical personnel as so desired, or in the alternative, can be retained within the structure of the nose bandage providing a solid member across the material 12.

The nose bandage geometrical structure includes opposing infra orbital trapezoidal portions 22 and 24, opposing side arms or wings 26 and 28, and a connecting bridge 30 therebetween. The opposing infra orbital portions 22 and 24 include opposing parallel orbital sides 32 and 34 and opposing outwardly curved sides 36 and 38 and 40 and 42. Likewise, the opposing side arms 26 and 28 of the trapezoidal geometrical shape include opposing parallel arm sides 44 and 46 and opposing outwardly curved sides 48 and 50 and 52 and 54. The arms can be a desired length.

While the illustrated nose bandage is not to be construed as limiting of the present invention, the gist of the present invention is a large section to adhere over the nose, a connecting bridge to go over the tip of the nose, and a smaller portion to cover over the nasal passages and up the sides of the nose. The connecting bridge includes opposing sides 56 and 58 and can be rectangular in shape.

FIG. 2 illustrates the nose bandage 10 where all numerals correspond to those elements previously described. Particularly illustrated is the structural relationship of the heights between the material 12, the adhesive coating 14, and the protective strip 16.

MODE OF OPERATION

Figure 3:
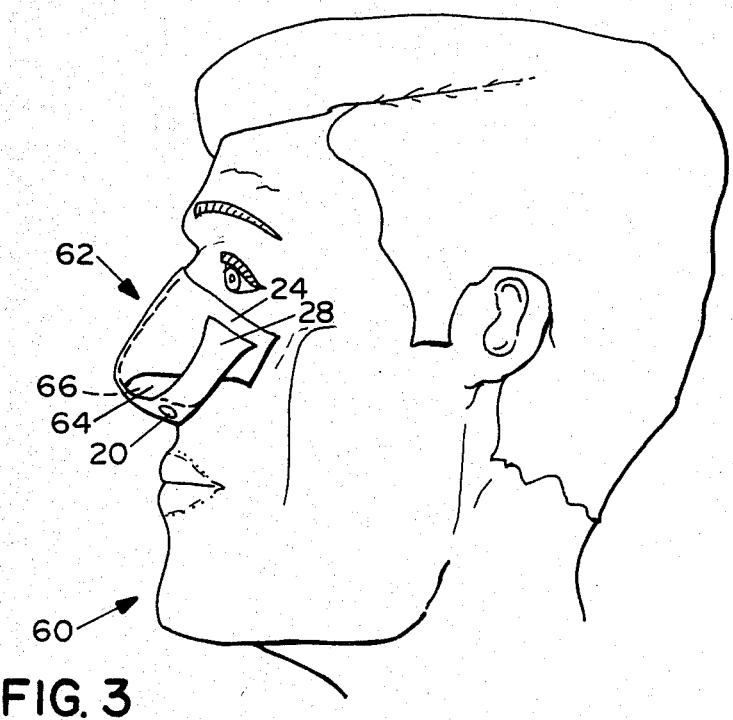
FIG. 3 illustrates a side view of a human face utilizing the nose bandage.
Figure 4:
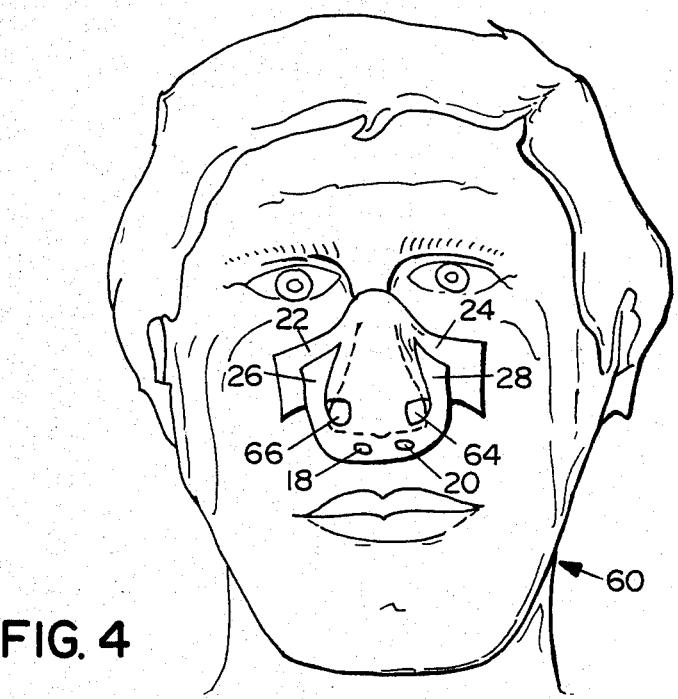
FIG. 4 illustrates a front view of a human face utilizing the nose bandage.

FIG. 3 illustrates a nose bandage 10 on a human face 60 and over the nose 62. Particularly illustrated is the overlapping of the side arm 28 over the infra orbital portion 24 leaving an open area 64 and a like corresponding open area 66, as illustrated in FIG. 4. It is also noted that a portion of each infra orbital portions 22 and 24 extends down over the check as illustrated in FIG. 3, but more so in FIG. 4. Small breathing passages are inherently provided in the open areas 64 and 66 in addition to the perforated holes 18 and 20.

I claim:
1. Nose bandage formed of a flexible material comprising:
   a. opposing infra orbital portion means of a predetermined trapezoidal like geometrical shape;
   b. opposing side arm means of trapezoidal like shape, the side arm means being smaller in geometrical size than said opposing infra orbital portion means;
   c. connecting bridge of a geometrical rectangular like shape between said opposing infra orbital portion means and said opposing side arm means in a mid portion thereof;
   d. at least two perforated nasal passage holes located in a substantially mid center portion of said side arm means; and,
   e. adhesive means with protective backing secured to one side of continuous material of said orbital portion means, said side arm means, said connecting bridge means, and said nose bandage means whereby said adhesive means secures said nose bandage about a nose of an individual thereby providing a one piece nose bandage for unilateral or bilateral nasal occlusions.

2. Nose bandage of claim 1 wherein said material is ⅛" foam.

3. Nose bandage of claim 1 wherein said material is adhesive material.

4. Nose bandage of claim 1 wherein said material is woven cloth.

5. Nose bandage of claim 1 wherein said material is plastic.

* * * * *

UNITED STATES PATENT AND TRADEMARK OFFICE
CERTIFICATE OF CORRECTION

PATENT NO. : 4,534,342
DATED : August 13, 1985
INVENTOR(S) : Charles Pexa

It is certified that error appears in the above-identified patent and that said Letters Patent is hereby corrected as shown below:

On the title page, the inventor's name should read

-- Charles Pexa --.

Signed and Sealed this

Twenty-second Day of July 1986

[SEAL]

Attest:

DONALD J. QUIGG

Attesting Officer

Commissioner of Patents and Trademarks